United States Patent
Borkan

(10) Patent No.: US 8,287,904 B2
(45) Date of Patent: Oct. 16, 2012

(54) STABLE SOFT CAPSULE DOSAGE FORM FOR ACETYLSALICYLIC ACID

(75) Inventor: Lionel Borkan, New Vernon, NJ (US)

(73) Assignee: Lionel Borkan, New Vernon, NJ (US)

( * ) Notice: Subject to any disclaimer, the term of this patent is extended or adjusted under 35 U.S.C. 154(b) by 0 days.

(21) Appl. No.: 12/859,389

(22) Filed: Aug. 19, 2010

(65) Prior Publication Data

US 2012/0045507 A1     Feb. 23, 2012

(51) Int. Cl.
*A61K 9/66* (2006.01)
*A61K 31/60* (2006.01)
*A61K 47/14* (2006.01)

(52) U.S. Cl. .......................... 424/455; 514/163; 514/786

(58) Field of Classification Search .................. None
See application file for complete search history.

(56) References Cited

U.S. PATENT DOCUMENTS

| 5,595,758 | A * | 1/1997 | Adusumilli et al. | 424/456 |
| 6,267,985 | B1 * | 7/2001 | Chen et al. | 424/451 |
| 6,383,471 | B1 * | 5/2002 | Chen et al. | 424/45 |
| 2008/0206323 | A1 * | 8/2008 | Zoppetti et al. | 424/463 |

* cited by examiner

*Primary Examiner* — David J Blanchard
*Assistant Examiner* — Tigabu Kassa
(74) *Attorney, Agent, or Firm* — Schwegman Lundberg Woessner, P.A.

(57) ABSTRACT

A stable soft gel dosage form for acetylsalicylic acid (ASA), aspirin, is provided wherein soft gel capsules containing the ASA can be stored for prolonged periods under typical home storage conditions with better than 98% or 99% ASA integrity and with negligible physical or chemical deterioration of the soft gelatin capsule over the period of six months. A suspension of ASA in a monoglyceride component comprising more than about 50% glyceryl monooleate is packaged in a soft gelatin capsule, which can be substantially free of other components. The ASA in this composition is resistant to hydrolysis from water contained within the soft gelatin matrix or diffusing through the matrix. Methods of preparation and methods of use are also provided.

21 Claims, No Drawings

STABLE SOFT CAPSULE DOSAGE FORM FOR ACETYLSALICYLIC ACID

BACKGROUND

Soft gelatin encapsulation of a solution or suspension of a pharmaceutical agent dissolved or suspended in a medium offers many advantages over other dosage forms such as compressed, coated or uncoated solid tablets, hard dried filled capsules, or bulk liquid preparations. Gelatin encapsulation of a solution or suspension permits accurate delivery of a unit dose. Such uniformity is more difficult to achieve via a tabletting process wherein solids must be uniformly mixed and compressed, or via incorporation of the total dose of active ingredient into a bulk liquid carrier which must be measured out prior to each oral administration. Soft gelatin capsules are also more easily transported by patients than bulk liquids, since only the required number of doses need be removed from the package.

Soft gelatin capsules are favored by many people for oral administration of medications, at least in part because of their ease of swallowing. The soft gelatin shell makes the capsule easier to swallow, especially for the elderly, than a tablet or a hard capsule. Furthermore, the contents of a soft gel capsule can be more bioavailable following ingestion due to rapid rupture of the capsule and release of the contents in the digestive tract. See, for example, U.S. Pat. Nos. 4,597,885, 4,708,834, 4,795,642 and 4,935,243 by the inventor herein.

However, soft gel capsules are formed of a gelatin and glycerol, wherein the capsule wall can be permeable to water vapor. The water can diffuse through the capsule wall into contact with a hydrolytically unstable drug contained within the capsule, causing hydrolysis.

Acetylsalicylic acid (ASA), or aspirin, is an example of a hydrolytically unstable drug. ASA is a commonly used analgesic and anti-inflammatory drug now often used in maintenance doses for prophylaxis of heart attacks and stroke, inhibition of blood coagulation, and prevention of thrombus and stenosis.

ASA has been commercially available in other dosage forms, such as coated or uncoated tablets, but instability of ASA to hydrolysis limits preparation of an oral dosage form that is stable for prolonged storage period sto formulations where the ASA is preserved in a substantially anhydrous state with barrier to contact with atmospheric moisture. A phenolic acetate, ASA hydrolyzes to an equimolar mixture of acetic acid and salicylic acid. These hydrolytic products bring about deleterious insolubilization of the soft gelatin capsule though the denaturing activity of the phenolic and acidic components, mainly salicylic acid.

Salts and buffered forms of ASA have been used, but these forms can act more slowly after ingestion than does ASA itself, and are not as effective as aspirin despite the various beneficial claims made.

Accordingly, there is a need for a formulation of ASA suitable for containment within soft gelatin capsules.

SUMMARY

The present invention is directed a dosage form comprising a formulation contained in a soft gelatin capsule ("soft gel cap") comprising acetylsalicylic acid (ASA), i.e., aspirin, in a liquid or semi-solid vehicle that is stable for a period of months, and consequently is suitable for consumer use of the soft capsule dosage form for oral self-administration of aspirin; to methods of making the dosage form; and to methods of using the dosage form.

In various embodiments, the invention provides a stable soft capsule dosage form for ASA, comprising a soft gelatin capsule, containing a suspension consisting essentially of an effective amount of the ASA, in solid form, in a monoglyceride component comprising at least about 50% glyceryl monooleate. In various embodiments the dosage form is substantially free of a base, a polyalkyleneoxide, a cellulose ether, a cyclodextrin, a polyvinylpyrrolidone, a metal ion, a crosslinking agent, a gelling agent, or an inorganic particulate material.

In various embodiments, the invention provides a method of preparing the dosage form of the invention, comprising:
(a) suspending solid acetylsalicylic acid in powder form in the monoglyceride component, substantially free of water, optionally with heating, to form an ASA suspension, and,
(b) encapsulating the ASA suspension in a soft gelatin capsule.

In various embodiments, the invention provides method of administering acetylsalicylic acid to a patient in need thereof, comprising orally ingesting one or more of the dosage form of the invention or a dosage form prepared by the method of the invention to the patient.

In various embodiments, the invention provides a kit for administration of the dosage form of the invention or a dosage form prepared by the method of the invention comprising a container comprising one or more of said dosage forms together with instructions for use, storage, or both, of the dosage form.

DETAILED DESCRIPTION

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

As used herein, "individual" or "patient" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The expression "effective amount", when used to describe therapy to an individual suffering from a disorder, refers to the amount of a compound of the invention that is effective to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

A "hydrolytically unstable drug" as the term is used herein refers to a chemical entity useful as a medicament for administration to a patient wherein the drug undergoes decomposition in the presence of water over a relevant period of time, i.e., weeks or months. An example is ASA.

A "soft gelatin capsule" or a "soft gel cap" or a "soft gelatin capsule" is a capsule formed predominantly of gelatin, glycerine, and water, that retains its solubility on prolonged storage. Soft gel caps are widely used for providing medicaments in a form for home storage and self-administration as needed. For example, ibuprofen soft gel caps are widely used. However, ibuprofen is not considered to be a hydrolytically unstable drug.

The term "stable soft capsule" as used herein refers to a capsule adapted for self-administration of ASA wherein the ASA does not significantly undergo hydrolysis upon storage for a period of some months, and wherein the soft gelatin capsule does not undergo significant insolubilization or denaturing, such as can occur due to the release of salicylic acid from hydrolysis of the ASA in the soft capsule. In various embodiments, the ASA-containing soft gel capsule does not undergo significant "tanning" or insolubilization when stored at about 25° C. and about 60% relative humidity (RH) for a period of six months.

"Acetylsalicylic acid" or "ASA", commonly known as aspirin, is a compound of the structure

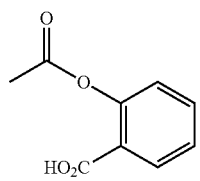

A "suspension" as the term is used herein refers to solid particles contained within a matrix of the monoglyceride component (and other optional components).

A "monoglyceride component" as the term is used herein refers to a composition that consists entirely or at least predominantly (at least greater than 90%) of one or more monoglyceride chemical species comprising at least about 50% of glyceryl monooleate, optionally further comprising other glyceryl monoesters such as glyceryl monoesters of the fatty acids palmitic, stearic, linoleic, linolenaic or gadoleic acid. A monoglyceride component can contain minor amounts of glycerol, diglycerides, and triglycerides, provided that one or more monoglyceride chemical species in the aggregate make up at least about 50% by weight of monoglyceride component.

Examples of useful monoglycerides include Myverol 18-92 (prepared from sunflower oil) and Myverol 18-99 (prepared from canola oil), which are termed distilled monoglycerides, developed by Eastman Chemical Products and now available from commercial suppliers. A monoglyceride can be a "distilled monoglyceride" as is known in the art. A distilled monoglyceride is a monoglyceride fraction that is prepared by transesterification of a triglyceride, such as a vegetable oil, with excess glycerol; or by esterification of glycerol with a fatty acid such as oleic acid optionally in the presence of a catalyst; then is purified by molecular distillation. A monoglyceride component of the present invention comprises a largely unsaturated fatty acid moiety such as an oleoyl moiety bonded to glycerol, either at the 1-position or at the 2-position of the glyceryl moiety.

Glyceryl monooleate is also known as "monoolein" CAS registry number 111-03-5. Another preparation commercially available is sold under the trade name of Capmul GMO or Capmul GMO-50, sold by Abitec Corp. of Columbus, Ohio, CAS registry number 25496-72-4, although from the specifications provided by the manufacturer, some lots may not meet the glyceryl monooleate specification herein.

"Substantially free of water" as the term is used herein refers to the suspension of the ASA in the monoglyceride component in preparation of the soft gel encapsulated dosage form of the invention having no added water; strictly anhydrous conditions are not to be inferred. Upon storage of the intact dosage form, the suspension may acquire some water content from the surrounding environment, e.g., humid air, diffusing through the gelatin capsule wall.

The present invention is directed to an oral dosage form of ASA (aspirin) suspended as a solid in a monoglyceride component, the suspension being contained in a soft gelatin capsule wherein the gelatin capsule shell comprises sufficient to avoid insolubilization of the gelatin, wherein the ASA is stable to hydrolysis over a period of at least about six months under conditions such as could be encountered in home medicine cabinet storage of the dosage form.

In various embodiments, the invention provides a stable soft capsule dosage form for ASA, comprising a soft gelatin capsule, containing a suspension consisting essentially of an effective amount of the ASA, in solid form, in a monoglyceride component comprising at least about 50% glyceryl monooleate. In various embodiments the dosage form is substantially free of a base, a polyalkyleneoxide, a cellulose ether, a cyclodextrin, a polyvinylpyrrolidone, a metal ion, a crosslinking agent, a gelling agent, or an inorganic particulate material.

In various embodiments, upon storage of the dosage form at about 25° C. and about 60% relative humidity, less than about 2% of the ASA undergoes hydrolysis over a period of six months. Example 1 and Table 1, below, shows stability data for a dosage form of the invention comprising an 80 mg ASA dose under these storage conditions, and demonstrate that less than about 2% hydrolysis of ASA, as determined by the content of salicylic acid detected over time, takes place. The average percentage decomposition determined in Example 1 based on ASA content after 6 months was 0.5%, and based on salicylic acid content was 0.9%. In various embodiments, less than about 1% of the ASA undergoes hydrolysis under the above-stated conditions over a period of six months.

In various embodiments, upon storage of the dosage form at about 25° C. and about 60% relative humidity, the soft gelatin capsule is substantially unchanged in solubility over a period of six months. When soft gelatin (glycerol can also be present) is exposed to the degradation products of ASA, acetic acid and salicylic acid, denaturation and hardening of the gelatin occurs. However, the inventive suspension of the ASA within the monosaccharide component serves to protect the ASA from hydrolysis. It is believed that monoglycerides such as are comprised by the monoglyceride component herein can form mesomorphic phases in water. For example, a cubic mesomorphic phase has been identified. See, for example, Esposito E, Eblovi N, Rasi S, Drechsler M, Di Gregorio G M, Menegatti E, Cortesi R. Lipid-Based Supramolecular Systems for Topical Application: A Preformulatory Study. *AAPS PharmSci.* 2003; 5 (4): article 30. DOI: 10.1208/ps050430. Exemplary monoglyceride components such as Myverol 18-92 and Myverol 18-99 can form such phases in the presence of water. The result can be a stable, clear gel which can fix up to about 35% water into the blend, forming what has been described as a cubic form. See Bodil Ericsson and Kare Larsson, *Zeitschriftfar Kristallographic* (1984), 168, 213-

219. This cubic phase can persist up to temperatures of about 85° C. and down to temperatures of about −40° C. It is believed by the inventors herein that the formation of the mesomorphic phase can serve to protect the ASA from hydrolysis by ambient water in the environment, such as from humid air, over the range of temperatures likely to be encountered in a home environment.

The monoglyceride component, which can be a mixture of chemical entities, but comprising at least about 50% of glyceryl monooleate (which can be a mixture of 1-substituted and 2-substituted forms), can also contain monoglycerides of other unsaturated or saturated fatty acids such as linoleic, linolenic, gadoleic, eicosenoic, palmitic, or stearic acids, and can also contain diglycerides, triglycerides, and glycerol. In various embodiments, the monoglyceride component can be a "distilled monoglyceride" as is known in the art, examples of which are Myverol 18-92, Myverol 18-99, and others. Such materials can be derived semisynthetically from oils, such as vegetable oils. See, for example, *J. Am Oil Chem. Soc.* (1979), 56, 751A. Processes include transesterification of triglycerides (the major component of vegetable oils) with glycerol, which can be present in an excess amount; the reaction can be catalyzed to bring about equilibration of acyl groups among all the glyceryl moieties present. Or, glycerol can be esterified, for example catalytically, with various fatty acids. Then, the mixture is molecularly distilled to provide the "distilled monoglyceride." This method of preparation can be used with sunflower oil, canola oil, corn oil, and the like, or a combination thereof.

In various embodiments, the monoglyceride component can comprise at least about 60% glyceryl monooleate. For example, the manufacturer's specification of Myverol 18-99 recites a glyceryl monooleate content of 60.9%. In various embodiments, the monoglyceride component can comprise at least about 65% glyceryl monooleate. For example, the manufacturer's specification for Myverol 18-92 recites a glyceryl monooleate content of 67.5%.

The person of ordinary skill in the art recognizes that a glyceryl monooleate chemical species can be either a 1-oleoylglycerol or a 2-oleoylglycerol. Using the standard nomenclature rules for glycerol, there cannot be a 3-oleoylglycerol as it is properly termed a 1-oleoylglycerol. In various embodiments of the invention, the glyceryl monooleate component comprises predominantly 1-oleoylglycerol. It is believed that a transesterification reaction using vegetable oil triglycerides and excess glycerol results in predominant formation of a 1-oleoylglycerol, which can be a result of kinetic factors in the reaction, primary hydroxyl groups typically being more reactive than secondary hydroxyl groups.

The ASA content of a soft capsule dosage form of the invention can contain any typically used dose of ASA. For example, doses of about 60 mg and of about 80 mg of ASA are commonly used prophylactically for prevention of heart disease and stroke. In various embodiments, each capsule contains about 60 mg, or about 80 mg, or about 100 mg, of ASA, or any amount in between. A dosage form capsule of the invention can further include larger ASA dosages. In various embodiments, an amount of ASA present in a capsule can range from about 50 mg to about 500 mg. A total capsule content can therefore be at least about 150 mg for 50 mg ASA at a 2:1 ratio of monoglyceride:ASA. At an ASA dose of 80 mg and a 4.5:1 ratio, the total capsule content is about 440 mg, see Example 1 below.

The ASA powder used in the dose form of the invention can be of any fineness consistent with ease of handling. The mixture of the ASA and monoglyceride component can be milled following suspension to prepare a more finely dispersed mixture. For example, in various embodiments, substantially all the ASA in solid form is a particulate of sufficient fineness to pass an 80 mesh screen.

An amount of monoglyceride component used relative to the amount of ASA should be sufficient to maintain flowability for filling the capsules. The ASA powder should also be of sufficient fineness to maintain flowability during filling operations.

The invention is further directed to a method of preparing a dosage form on the invention, comprising:

(a) suspending solid acetylsalicylic acid in powder form in the monoglyceride component, substantially free of water, optionally with heating, to form an ASA suspension, and, (b) encapsulating the ASA suspension in a soft gelatin capsule.

The dosage form of the invention can be prepared by any method suitable for the filling of soft gelatin capsules. See, for example, Remington: *The Science and Practice of Pharmacy*, 19th Ed., 1995, or later versions thereof, incorporated by reference herein.

In various embodiments, when suspending the ASA, the monoglyceride component can be in form a neat melt at an elevated temperature, for example above about 41° C. In various embodiments, the suspension can then being milled to provide a suspension of the ASA suitable to pass an 80 mesh screen. In various embodiments, following formation of the ASA suspension, a step of degassing under vacuum is employed.

In various embodiments, after encapsulating the ASA suspension, upon cooling to room temperature, the suspension cools to form a paste or semi-liquid. In various embodiments, encapsulation is carried out using a rotary die encapsulator.

In various embodiments, the invention provides a kit for administration of the dosage form of the invention or a dosage form prepared by the method of the invention comprising a container enclosing one or more of said dosage forms together with instructions for use, storage, or both, of the dosage forms. For example, a plurality of the soft capsules can be packaged in a labeled screwtop or snaptop plastic jar. Alternatively, each individual soft capsule can be bubble-packed in a plastic individual foil and/or plastic wrapper for unpacking by the patient immediately prior to use. Any method of packaging can include dosage and side-effect information and storage and disposal directions.

In various embodiments, the invention provides a method of administering acetylsalicylic acid to a patient in need thereof, comprising orally ingesting one or more of the dosage form of the invention or a dosage form prepared by the method of the invention to the patient. ASA is a well known medicament and is available over the counter. A patient can self-administer the dosage form in any needed quantity at any location, e.g., at home, at work, etc. The dosage form can be self-administered for treatment of pain or inflammation, for inhibiting blood coagulation, and prevention of thrombus or stenosis within a blood vessel, or for any other known therapeutic value of ASA.

EXAMPLES

Example 1

Preparation of a Soft Gel Capsule and Evaluation of Storage Stability

Acetylsalicylic acid (ASA), 80 mg, in powder form, was suspended in a monoglyceride component (Myverol 18-92, 360 mg) and encapsulated in a 7.5 minim oval soft gelatin capsule formed of gelatin with glycerol and dyes, to provide a dosage form of the invention.

Ten substantially identical capsules were stored under conditions of 25° C. and 60% relative humidity (RH), approximately conditions expected to be encountered in home medicine cabinet storage of the capsules, for a period of six months.

At the end of the six month period, each capsule was quantitatively analyzed by gas chromatography using flame ionization detection for ASA and for salicylic acid. The results are provided in Table 1, below.

TABLE 1

Stability of ASA oral dosage form of the invention

| Capsule # | Original ASA mg | ASA Content/ 6 months | Salicylic Acid Content/6 months |
|---|---|---|---|
| 1 | 80.00 | 79.84 | 0.92 |
| 2 | 80.00 | 79.74 | 1.09 |
| 3 | 80.00 | 80.03 | 0.32 |
| 4 | 80.00 | 79.09 | 0.68 |
| 5 | 80.00 | 79.36 | 0.24 |
| 6 | 80.00 | 79.60 | 0.52 |
| 7 | 80.00 | 79.64 | 1.12 |
| 8 | 80.00 | 79.35 | 0.31 |
| 9 | 80.00 | 79.88 | 0.88 |
| 10 | 80.00 | 79.68 | 0.92 |

The average ASA content at six months was 79.62±0.20 mg (99.53%±0.25%), relative deviation for 95% is 0.25%. The average salicylic acid content at 6 months was 0.70±0.23 mg (0.88%±0.28%).

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A stable soft capsule dosage form for acetylsalicylic acid consisting essentially of an effective amount of the acetylsalicylic acid, in solid form, in a monoglyceride component comprising at least about 50% glyceryl monooleate, wherein the dosage form is substantially free of a base.

2. The dosage form of claim 1 wherein upon storage of the dosage form at about 25° C. and about 60% relative humidity, less than about 2% of the acetylsalicylic acid undergoes hydrolysis over a period of six months.

3. The dosage form of claim 1 wherein upon storage of the dosage form at about 25° C. and about 60% relative humidity, less than about 1% of the acetylsalicylic acid undergoes hydrolysis over a period of six months.

4. The dosage form of claim 1 wherein upon storage of the dosage form at about 25° C. and about 60% relative humidity, the soft gelatin capsule does not undergo significant hardening over a period of six months.

5. The dosage form of claim 1 wherein the monoglyceride component comprises a distilled monoglyceride.

6. The dosage form of claim 1 wherein the monoglyceride component is derived from a vegetable oil.

7. The dosage form of claim 6 wherein the vegetable oil is sunflower oil, canola oil, or a combination thereof.

8. The dosage form of claim 1 wherein the monoglyceride component comprises at least about 60% glyceryl monooleate.

9. The dosage form of claim 1, wherein the monoglyceride component comprises at least about 65% glyceryl monooleate.

10. The dosage form of claim 1 wherein the glyceryl monooleate component comprises predominantly a 1-oleoylglycerol.

11. The dosage form of claim 1 wherein an amount of acetylsalicylic acid present in a capsule ranges from about 50 mg to about 500 mg.

12. The dosage form of claim 1 wherein substantially all the acetylsalicylic acid in solid form is a particulate of sufficient fineness to pass an 80 mesh screen.

13. A method of preparing the dosage form of claim 1, comprising: (a) suspending solid acetylsalicylic acid in powder form in the monoglyceride component comprising at least about 50% glyceryl monooleate, substantially free of water, optionally with heating, to form an acetylsalicylic acid suspension, and, (b) encapsulating the acetylsalicylic acid suspension, substantially free of a base, in a soft gelatin capsule.

14. The method of claim 13 wherein when suspending the acetylsalicylic acid, the monoglyceride component is in form a neat melt at an elevated temperature.

15. The method of claim 13 wherein the suspension of the acetylsalicylic acid in the monoglyceride component is milled to provide a suspension of the acetylsalicylic acid suitable to pass an 80 mesh screen.

16. The method of claim 14 wherein after encapsulating the acetylsalicylic acid suspension, upon cooling to room temperature, the suspension is in form of a paste or semi-liquid.

17. The method of claim 13 wherein following formation of the acetylsalicylic acid suspension, a step of degassing under vacuum is employed.

18. The method of claim 13 wherein encapsulation is carried out using a rotary die encapsulating machine.

19. A method of administering acetylsalicylic acid to a patient in need thereof, comprising orally ingesting one or more of the dosage form of claim 1 or a dosage form prepared by the method of claim 13 to the patient.

20. The method of claim 19 wherein the acetylsalicylic acid is administered to the patient for treatment of pain or inflammation, for inhibiting blood coagulation and prevention of thrombus or stenosis within a blood vessel.

21. A kit for administration of the dosage form of claim 1 or a dosage form prepared by the method of claim 13 comprising a container comprising one or more of said dosage forms together with instructions for use, storage, or both, of the dosage forms.

* * * * *